US007563268B2

(12) United States Patent
Ishikawa

(10) Patent No.: US 7,563,268 B2
(45) Date of Patent: Jul. 21, 2009

(54) TROCAR SYSTEM

(75) Inventor: Manabu Ishikawa, Akiruno (JP)

(73) Assignee: Olympus Corporation (JP)

( * ) Notice: Subject to any disclaimer, the term of this patent is extended or adjusted under 35 U.S.C. 154(b) by 1143 days.

(21) Appl. No.: 10/737,258

(22) Filed: Dec. 15, 2003

(65) Prior Publication Data
US 2004/0153053 A1 Aug. 5, 2004

(30) Foreign Application Priority Data
Dec. 16, 2002 (JP) .............................. 2002-363968

(51) Int. Cl.
A61B 17/22 (2006.01)
(52) U.S. Cl. ..................................... 606/167
(58) Field of Classification Search ................ 606/167, 606/184, 164.11, 264, 164.01, 185, 169, 606/171, 79; 600/437, 464, 471, 562–572, 600/37; 623/2.11; 604/272, 264, 164.1, 604/164.11; 433/165; 27/24.1
See application file for complete search history.

(56) References Cited
U.S. PATENT DOCUMENTS 4,535,759 A * 8/1985 Polk et al. ...................... 601/2
4,573,448 A * 3/1986 Kambin ...................... 606/170
4,655,750 A * 4/1987 Vaillancourt ............ 604/165.01
4,981,482 A * 1/1991 Ichikawa ..................... 606/108
4,994,027 A * 2/1991 Farrell ........................ 604/510
5,385,562 A * 1/1995 Adams et al. ................ 604/528
5,746,720 A * 5/1998 Stouder, Jr. ................. 604/117
5,976,115 A * 11/1999 Parris et al. ................. 604/533
5,993,408 A * 11/1999 Zaleski ......................... 604/22
6,013,046 A * 1/2000 Maaskamp et al. ............ 604/22

FOREIGN PATENT DOCUMENTS
JP 5-57863 8/1993
JP 2002-177293 6/2002

* cited by examiner

Primary Examiner—Kevin T Truong
(74) Attorney, Agent, or Firm—Ostrolenk, Faber, LLP

(57) ABSTRACT

A trocar system includes a probe, a sheath, a dilator, a trocar, an engaging mechanism, and a hold portion. The probe is inserted in a through hole of the sheath. The dilator includes a dilating portion to dilate the punctured hole formed by the probe. The sheath is inserted in the through hole of the dilator. The dilator is inserted in the through hole of the trocar. After the trocar is guided into the punctured hole, the probe, sheath, and dilator are removed from the through hole of the trocar, and the trocar is retained in a body wall. The engaging mechanism detachably engages the trocar with the dilator. In a state in which the dilator is inserted in the trocar and the engaging mechanism engages the trocar with the dilator, the base ends of the trocar and dilator are integrated with each other by the hold portion.

55 Claims, 5 Drawing Sheets

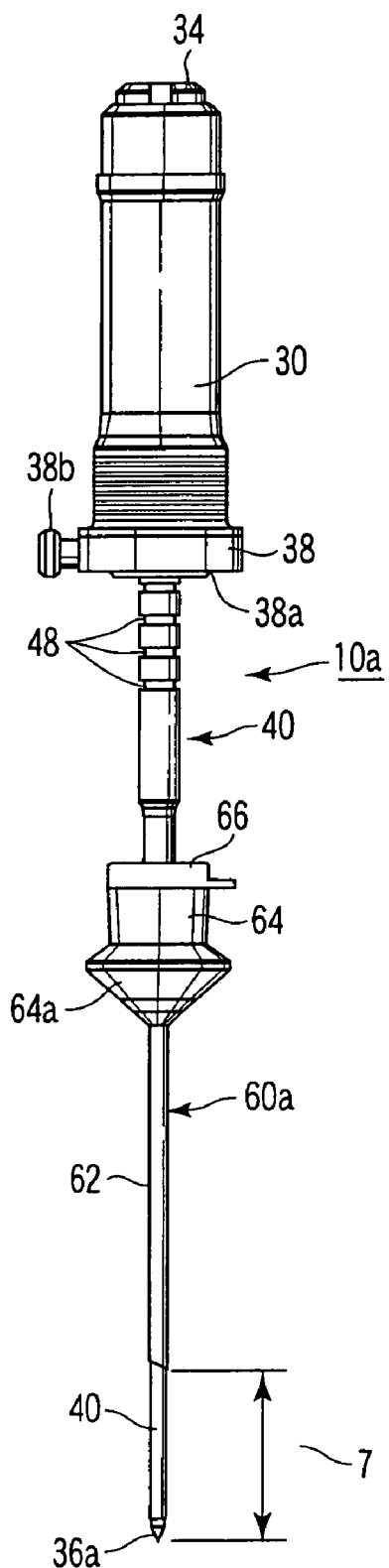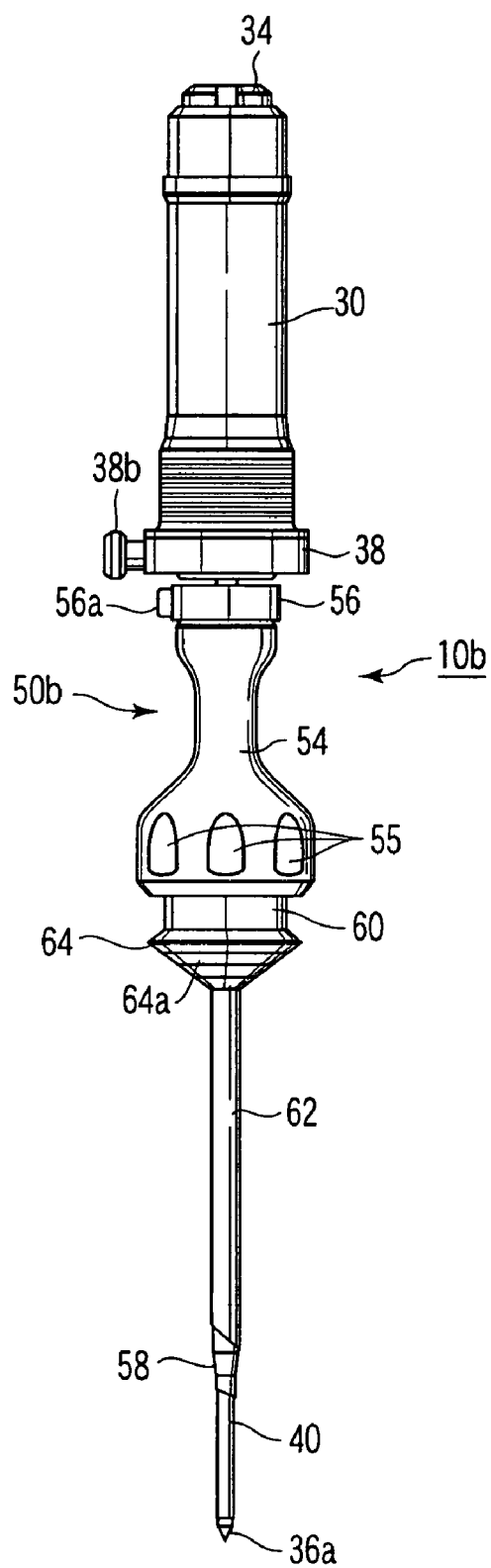
FIG. 4
FIG. 6

TROCAR SYSTEM

CROSS-REFERENCE TO RELATED APPLICATIONS

This application is based upon and claims the benefit of priority from the prior Japanese Patent Application Ser. No. 2002-363968, filed Dec. 16, 2002,the entire contents of which are incorporated herein by reference.

BACKGROUND OF THE INVENTION

1. Field of the Invention

The present invention relates to a trocar system for inserting and retaining a trocar for use as a guide tube of an insertion instrument into a body cavity into a patient's body wall.

2. Description of the Related Art

In a trocar system, for example, a probe including a sharp puncturing needle on a tip end, and a trocar which is disposed in an outer periphery of the probe and which is to be inserted and retained in a patient are detachably combined. The trocar system is stuck into the patient's body wall and guided into a body cavity in a state in which the probe and trocar are integrally combined. When the probe is detached from the trocar in this state, only the trocar is retained in the body wall. This trocar is used as a guide tube in a scope for observing various lesioned parts and a treatment instrument for performing a treatment.

Various modes of the trocar system have heretofore been known. For example, in Jpn. Pat. Appln. KOKOKU Publication No. 5-57863, an ultrasonic trocar system has been disclosed. For the ultrasonic trocar system, the probe is ultrasonically vibrated in the state in which the probe is integrally combined with the trocar, and a punctured hole can be formed in the patient's body wall. As a result, the probe can safely be stuck and guided into the body wall with a comparatively light force by the ultrasonic vibration. The trocar can also be guided into the body wall following the probe. The probe is detached from the trocar, and the trocar is retained in the body wall.

In Jpn. Pat. Appln. KOKAI Publication No. 2002-177293, an improved ultrasonic trocar system has been disclosed. For this ultrasonic trocar system, a dilator whose tip end is formed to be tapered substantially in a conical shape is disposed between the trocar and the probe whose outer diameter is comparatively small. In this system, the tapered tip end of the dilator projects from the tip end of the trocar. The tip end of the probe projects from the tapered tip end of the dilator. In the ultrasonic trocar system in this state, the probe is ultrasonically vibrated and guided into the patient's body wall. Thereafter, an operator holds the dilator and trocar, and dilates a cavity in the patient's body wall with the trocar. Then, the trocar system is guided into the body wall. Thereafter, the probe and dilator are removed from the trocar to retain the trocar in the body wall.

BRIEF SUMMARY OF THE INVENTION

According to one aspect of the present invention, there is provided a trocar system including a probe which forms a punctured hole in a living tissue, a sheath, a dilator, a trocar, an engaging mechanism, and a hold portion. The probe is inserted in a through hole of the sheath. The dilator includes a dilating portion to dilate the punctured hole formed in the living tissue by the tip end of the probe in the tip end of the dilator. The sheath is inserted in the through hole of the dilator. The dilator is inserted in the through hole of the trocar. After the trocar between the tip and base ends is guided into the punctured hole, the probe, sheath, and dilator are removed from the through hole of the trocar, and the trocar is retained in a patient's body wall. The engaging mechanism detachably engages the trocar with the dilator. In a state in which the dilator is inserted in the trocar and the engaging mechanism engages the trocar with the dilator, the base ends of the trocar and dilator are integrated with each other by the hold portion.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 4 is a schematic diagram showing the ultrasonic trocar system according to a second embodiment;

FIG. 6 is a schematic diagram showing the ultrasonic trocar system according to a third embodiment;

DETAILED DESCRIPTION OF THE INVENTION

Preferred embodiments of the present invention will hereinafter be described with reference to the drawings.

Figure 1:
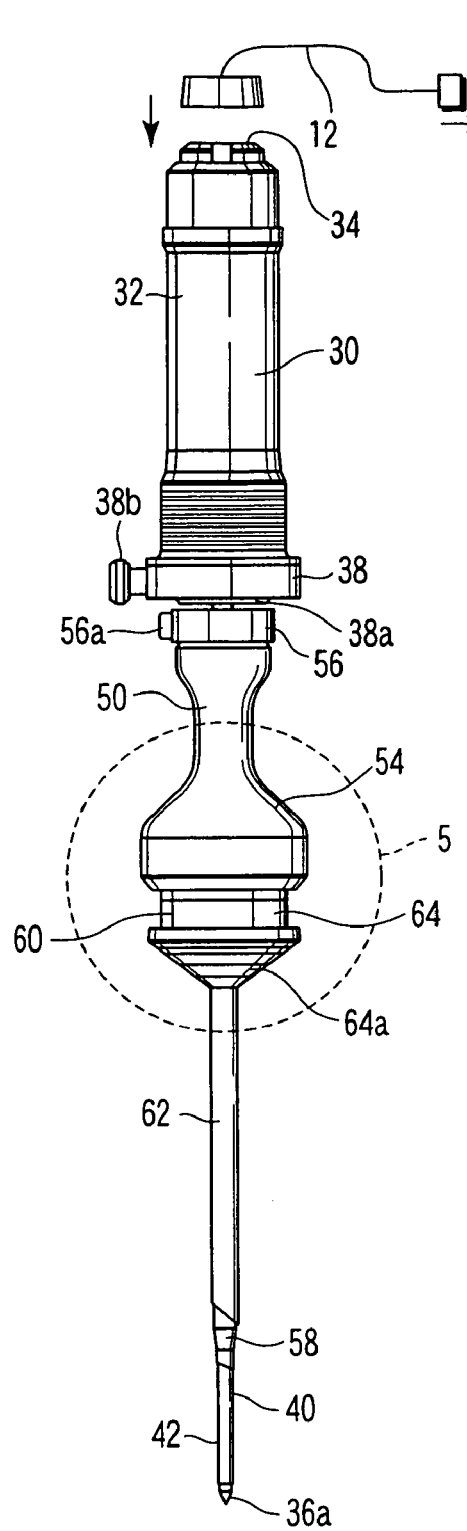
FIG. 1 is a schematic diagram showing an ultrasonic trocar system according to a first embodiment.
Figure 2:
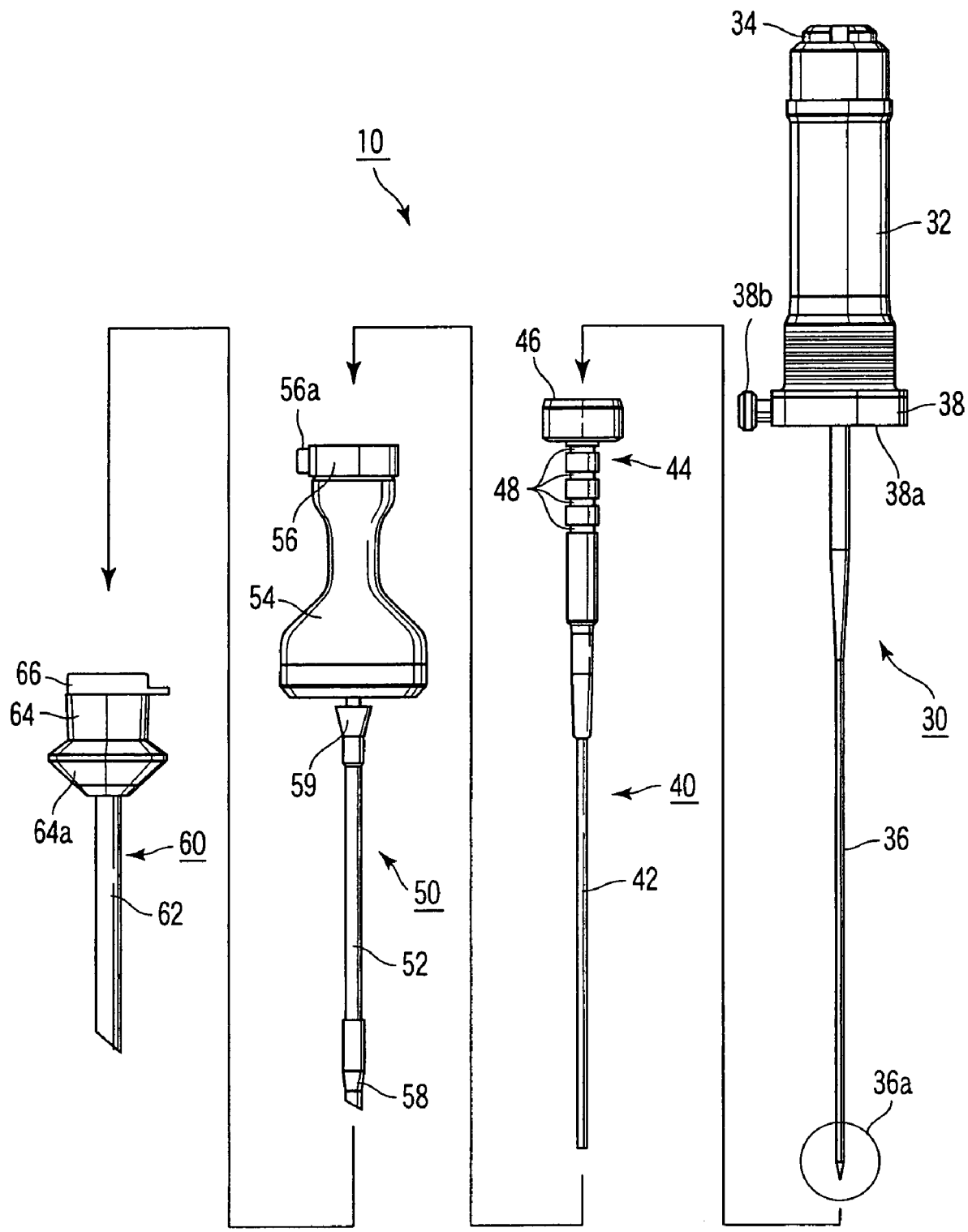
FIG. 2 is a schematic exploded view of the ultrasonic trocar system according to the first embodiment.

First, an ultrasonic trocar system 10 according to a first embodiment will be described with reference to FIGS. 1 to 3B. FIG. 1 shows a constitution of the ultrasonic trocar system 10 according to the present embodiment. FIGS. 2 to 3B further concretely show the constitution of the ultrasonic trocar system 10 shown in FIG. 1.

As shown in FIGS. 1 and 2, the ultrasonic trocar system 10 according to the present embodiment includes a handpiece unit 30, sheath 40, dilator 50, and trocar 60. As shown in FIG. 1, the handpiece unit 30 is connected to a power source device 14 via a cable 12. The power source device 14 is connected to switches 16 which output a signal for operating the power source device 14, such as a foot switch and a hand switch. When a predetermined signal is inputted into the power source device 14 via the switch 16, the power source device 14 supplies a power to an ultrasonic vibrator described later.

As shown in FIG. 2, the handpiece unit 30 includes an ultrasonic transducer 32 and a probe 36. The ultrasonic transducer 32 includes a piezoelectric device (not shown) which is an ultrasonic vibrator, and a conical horn (not shown) which is connected to the piezoelectric device to enlarge ultrasonic vibration generated by the piezoelectric device. A base end (upper end) of the transducer 32 is connected to a connector portion 34 connected to the other end of the cable 12 whose one end is connected to the power source device 14. Therefore, it is possible to supply a power to the piezoelectric device from the power source device 14 via the cable 12.

The tip end (lower end) of the horn is detachably connected to the base end (upper end) of the elongated probe 36 constituted of a linear needle member which is capable of transmitting the ultrasonic vibration and which is to be stuck to the body wall, for example, via screws. That is, the probe 36 includes a linear shaft (central shaft). The handpiece unit 30 is capable of further enlarging the ultrasonic vibration generated by the piezoelectric device of the ultrasonic transducer 32 and transmitted to and enlarged by the horn to transmit the vibration to the tip end (lower end) of the probe 36.

Figure 3A:
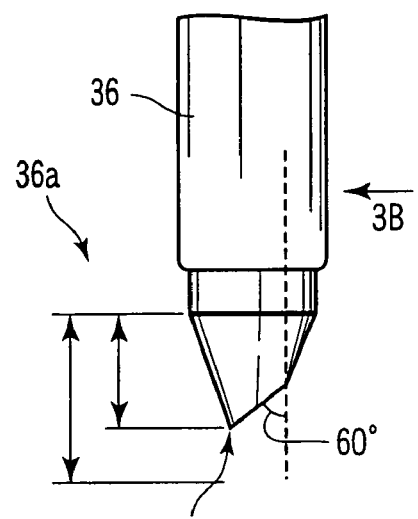
FIG. 3A is a schematic diagram of a tip end of the ultrasonic trocar system according to the first embodiment.
Figure 3B:
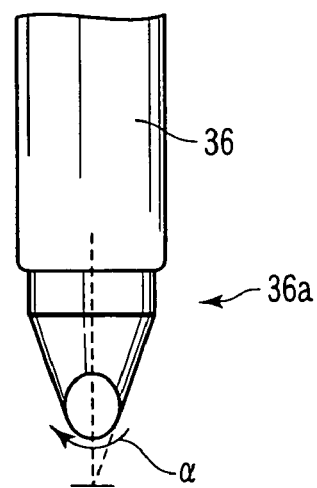
FIG. 3B is a schematic diagram of the tip end of the ultrasonic trocar system according to the first embodiment seen from a direction of an arrow 3B shown in FIG. 3A.

As shown in FIGS. 3A and 3B, a portion of a tip end (needle portion) 36*a* of the probe 36 in the vicinity of a vertex portion of a substantially conical shape is cut with respect to the shaft of the probe 36 by an appropriate angle, that is, by a surface of 60 degrees in this embodiment. Therefore, a ridge line (edge) of a substantially elliptic shape is formed on the tip end 36*a* of the probe 36. Since the tip end 36*a* of the probe 36 is cut, the tip end 36*a* of the probe 36 can be reduced in length. The tip end 36*a* of the probe 36 can have an obtuse shape as compared with the conical shape before cut. A cut angle of the tip end 36*a* of the probe 36 with respect to the axis of the probe 36 is 60 degrees or less which is preferably the same as or larger than a vertical angle of the substantially conical shape of the tip end 36*a*.

When the cut angle is set to 60 degrees or less with respect to the axis of the probe 36, and when the tip end 36*a* of the probe 36 is stuck into the body wall, many cavitations are generated toward the axial direction of the probe 36 under peritoneum, and there is a possibility that it becomes more difficult to pass the tip end through the peritoneum. On the other hand, when the cut angle is 60 degrees or more, it is difficult to incise a tissue, peritoneum, and the like without any ultrasonic vibration. However, the incision is sharply started, when the ultrasonic vibration is performed.

A portion denoted with character a on the tip end 36*a* of the probe 36 does not have an acute angle, and preferably has a certain obtuse shape. Therefore, the handling of the probe during preparation is comparatively safe, and operator's hand and fingers are prevented from being damaged.

The tip end (lower end) of the ultrasonic transducer 32 includes a lock mechanism portion 38 disposed to engage the handpiece unit 30 with the base end (upper end) of the sheath 40. The lock mechanism portion 38 includes a disc-shaped concave portion 38*a* which is symmetric with respect to the axis of the probe 36, and an engaging pin 38*b* in a direction crossing at right angles to the axial direction of the probe 36. A handpiece unit fitting member 46 described later is fitted in the concave portion 38*a*. The engaging pin 38*b* is urged in a direction apart from the probe 36, for example, via a spring, in a direction crossing at right angles to the axial direction of the probe 36. When the operator pushes in and rotates the engaging pin 38*b* in the vicinity of the probe 36, the engaging pin 38*b* is engaged with the lock mechanism portion 38 (see FIG. 7).

As shown in FIG. 2, the sheath 40 includes an elongated cylindrical probe insertion portion 42 in which the probe 36 is disposed, and an engaging portion 44 disposed on the base end (upper end) of the probe insertion portion 42. The probe insertion portion 42 is linearly formed, and includes a through hole extending to the upper end from the lower end on a central axis. The hole extends to the upper end of the engaging portion 44 from the lower end of the probe insertion portion 42 on the central axis of the probe insertion portion 42 and engaging portion 44 so that the probe 36 is disposed in the hole. That is, the engaging portion 44 has a through hole communicating with that of the cylindrical probe insertion portion 42. When the probe 36 of the handpiece unit 30 is disposed in the through hole, the probe insertion portion 42 substantially entirely contacts to an outer peripheral surface of the probe 36 excluding the tip end 36*a* of the probe 36. Especially, the probe insertion portion 42 is formed of a material having a heat resistance and good slipping property, such as PTFE, because the portion directly contacts the probe 36 vibrating to generate heat.

The engaging portion 44 includes the handpiece unit fitting member 46 to be fitted into the concave portion 38*a* of the lock mechanism portion 38, and dilator fitting grooves 48 to be engaged with a lock mechanism portion 56 of the dilator 50 described later. The dilator fitting grooves 48 are formed in the outer peripheral surface of the base end of the probe insertion portion 42. The handpiece unit fitting member 46 is fitted into the concave portion 38*a* of the lock mechanism portion 38, and engaged with the engaging pin 38*b* (locked). Therefore, the handpiece unit 30 is attached to the sheath 40.

The dilator 50 includes an elongated cylindrical sheath insertion portion 52 in which the probe insertion portion 42 of the sheath 40 is disposed and a first hold portion 54 which is disposed on the base end (upper end) of the sheath insertion portion 52 and which is to be held by the operator. The sheath insertion portion 52 includes a through hole linearly formed and extending to the upper end from the lower end on the central axis. The hole extends to the upper end of the first hold portion 54 from the lower end of the sheath insertion portion 52 on the central axis of the sheath insertion portion 52 and first hold portion 54 so that the probe insertion portion 42 is disposed in the hole. That is, the first hold portion 54 has a through hole communicating with that of the cylindrical sheath insertion portion 52. When the probe insertion portion 42 of the sheath 40 is disposed in the through hole, the sheath insertion portion 52 substantially entirely contacts to the outer peripheral surface of the probe insertion portion 42 excluding the tip end of the probe insertion portion 42.

The lock mechanism portion 56 for engaging with the dilator fitting grooves 48 of the sheath 40 is disposed on the base end (upper end) of the first hold portion 54. A lower end surface of the handpiece unit fitting member 46 abuts on an upper end surface of the lock mechanism portion 56, and an engaging pin 56*a* for engaging with the dilator fitting grooves 48 of the sheath 40 is disposed in a direction crossing at right angles to the axial direction of the probe 36. The engaging pin 56*a* is urged in the direction apart from the probe 36, for example, via the spring, in the direction crossing at right angles to the axial direction of the probe 36. When the operator pushes in and rotates the engaging pin 56*a* in the vicinity of the probe 36, the engaging pin 56*a* is engaged with the lock mechanism portion 56. Therefore, the sheath 40 is engaged (locked), when the engaging pin 56*a* of the lock mechanism portion 56 of the dilator 50 is disposed in any one of the dilator fitting grooves 48.

A concave portion (not shown) in which a second hold portion 64 of the trocar 60 including a rubber seal member 66 of the trocar 60 described later is fitted is formed in the tip end (lower end) of the first hold portion 54.

A diameter in the vicinity of the tip end (lower end) of the sheath insertion portion 52 is slightly smaller than an inner diameter of a dilator insertion portion 62 described later. A punctured hole dilating portion 58 having an inner diameter which is slightly larger than the outer diameter of the probe insertion portion 42 is disposed on the outer peripheral surface of the tip end of the sheath insertion portion 52. A protrusion 59 which is easily engaged with the rubber seal member 66 of the trocar 60 described later is disposed on the outer peripheral surface of the base end of the sheath insertion portion 52.

The first hold portion 54 is processed in a shape including a curved surface which is easily grasped by the operator. Concretely, the portion is formed in such a manner that the diameter of the portion is reduced in a smooth curved surface state toward a middle portion of the hold portion 54 from the upper end on which the lock mechanism portion 56 is disposed as the base end of the hold portion 54. The portion is formed in such a manner that the diameter of the portion is enlarged in the curved surface state toward a side on which the sheath insertion portion 52 is disposed as the tip end (lower end) of the hold portion 54 from the middle portion of the hold portion 54. For example, the diameter of the tip end of the hold portion 54 is preferably larger than that of the base end. That is, the hold portion 54 of the dilator 50 includes large diameter portions on the upper and lower ends, and a constricted portion (small diameter portion) is disposed between these large diameter portions. In this manner, the first hold portion 54 of the dilator 50 is formed, for example, substantially in a gourd shape. The constricted portion is held, for example, with the operator's thumb and index finger. The lower-end large diameter portion is held, for example, by the operator's palm.

Next, the trocar 60 will be described. The trocar 60 includes an elongated cylindrical dilator insertion portion 62 in which the sheath insertion portion 52 of the dilator 50 is disposed, and a second hold portion 64 which is disposed on the base end (upper end) of the insertion portion 62 and which is to be held by the operator. The dilator insertion portion 62 is a portion to be retained in the body wall by a friction between the outer peripheral surface of the dilator insertion portion 62 and the body wall. The dilator insertion portion 62 is linearly formed, and includes a through hole extending to the upper end from the lower end on the central axis. The hole extends to the upper end of the second hold portion 64 from the lower end of the dilator insertion portion 62 on the central axis of the dilator insertion portion 62 and second hold portion 64 so that the sheath insertion portion 52 of the dilator 50 is disposed in the hole. That is, the second hold portion 64 has a through hole communicating with that of the cylindrical sheath insertion portion 52. When the sheath insertion portion 52 of the dilator 50 is disposed in the through hole, the dilator insertion portion 62 substantially entirely contacts to the outer peripheral surface of the sheath insertion portion 52 excluding the punctured hole dilating portion 58 of the tip end of the dilator 50.

The second hold portion 64 includes a bulging portion 64a bulging substantially in a conical shape toward the base end of the second hold portion 64 from the base end of the dilator insertion portion 62 (the tip end of the second hold portion 64) in a direction crossing at right angles to the axial direction of the dilator insertion portion 62. The rubber seal member 66 formed of a flexible material, such as a rubber material, is detachably attached to the base end of the hold portion 64. The through hole is formed in the middle portion of the rubber seal member 66 so that the protrusion 59 of the dilator 50 is easily engaged with the member.

Next, an assembly operation of assembling the ultrasonic trocar system 10 constituted in this manner will be described.

The tip end 36a of the probe 36 of the handpiece unit 30 is inserted into the probe insertion portion 42 via the engaging portion 44 on the base end of the sheath 40. The handpiece unit fitting member 46 of the sheath 40 is fitted in the concave portion 38a of the lock mechanism portion 38 of the ultrasonic transducer 32. The engaging pin 38b engages with the handpiece unit fitting member 46 disposed in the concave portion 38a. At this time, the inner peripheral surface of the probe insertion portion 42 closely contacts to the outer peripheral surface of the probe 36. The handpiece unit 30 is engaged with the sheath 40 in this manner.

The tip end of a unit obtained by assembling the handpiece unit 30 and sheath 40 is inserted into the sheath insertion portion 52 via the lock mechanism portion 56 of the base end of the dilator 50. The upper end surface of the lock mechanism portion 56 of the dilator 50 is allowed to abut on the lower end surface of the handpiece unit fitting member 46 of the sheath 40. The engaging pin 56a of the lock mechanism portion 56 of the dilator 50 is engaged with one of the dilator fitting grooves 48 of the sheath 40. At this time, the inner peripheral surface of the sheath insertion portion 52 closely contacts to the outer peripheral surface of the probe insertion portion 42. Therefore, the sheath 40 is engaged with the dilator 50. Then, the handpiece unit 30, sheath 40, and dilator 50 are engaged with one another.

The tip end of a unit assembled in this manner is inserted into the dilator insertion portion 62 from the rubber seal member 66 of the base end of the hold portion 64 of the trocar 60. When the protrusion 59 of the dilator 50 is inserted in the hole in the middle portion of the rubber seal member 66 of the trocar 60, the dilator is engaged with the trocar by an elastic force of the rubber seal member 66. Therefore, the dilator 50 is engaged with the trocar 60. At this time, the inner peripheral surface of the dilator insertion portion 62 substantially closely contacts to the outer peripheral surface of the probe insertion portion 42. Then, the handpiece unit 30, sheath 40, dilator 50, and trocar 60 are engaged with one another in one united body.

That is, the inner diameter of the probe insertion portion 42 of the sheath 40 is slightly larger than the outer diameter of the probe 36. The inner diameter of the sheath insertion portion 52 of the dilator 50 is slightly larger than the outer diameter of the probe insertion portion 42. The inner diameter of the dilator insertion portion 62 of the trocar 60 is slightly larger than the outer diameter of the sheath insertion portion 52. The outer peripheral surface of the sheath insertion portion 52 of the dilator 50 is formed slidably with the inner peripheral surface of the dilator insertion portion 62 of the trocar 60.

At this time, the tip end 36a of the probe 36 is disposed in an endmost (lowermost) position of the ultrasonic trocar system 10. The tip end of the probe insertion portion 42, the tip end (punctured hole dilating portion 58) of the sheath insertion portion 52, and the tip end of the dilator insertion portion 62 are arranged in order toward the base end from the tip end of the probe 36.

In this manner, the ultrasonic trocar system 10 shown in FIG. 1 is formed. The connector portion 34 of the handpiece unit 30 of the ultrasonic trocar system 10 is connected to the power source device 14 and switch 16 via the cable 12.

The operator simultaneously grasps a portion shown by a broken line and denoted with reference numeral 5, that is, the first hold portion 54 and second hold portion 64, ultrasonically oscillates the system, and pierces the body wall to form the punctured hole. This shape is very easily held by the operator, and is formed using human engineering in a shape capable of minutely controlling a force at the time of the piercing or handling an abrupt accident at the time of occurrence.

Concretely, the operator holds the constricted portion of the first hold portion 54 with the thumb and index finger as if a loop were made. The operator holds the large diameter portion of the lower end of the first hold portion 54 by the palm. The operator attaches the little finger to the conical bulging portion 64a of the lower end of the second hold portion 64. The middle finger is attached, for example, to the lower end of the first hold portion 54. The third finger is attached, for example, to the upper end of the second hold portion 64.

Since the operator can grasp both the first hold portion 54 and the second hold portion 64 with one hand in one united body, a positional relation between the dilator 50 and the trocar 60 is stabilized, that is, the ultrasonic trocar system 10 is stabilized. Therefore, the force can finely be controlled at the time of the piercing, or the abrupt accident can momentarily and easily be handled at the time of the occurrence.

The operator can grasp the first and second hold portions 54, 64 in a desired grasping manner. For example, the operator's finger (e.g., the middle or third finger) may also be attached to a position (stepped position) of the second hold portion 64 between the upper end surface of the bulging portion 64a of the second hold portion 64 and the lower end surface of the first hold portion 54.

Next, an operation method (function) of the ultrasonic trocar system 10 will be described.

When the switch 16 as input means for operating an output control mechanism of the power source device 14 is operated, an electric energy is supplied to the piezoelectric device of the transducer 32 from the power source device 14. The piezoelectric device generates mechanical vibration in accordance with the energy amount, amplifies this vibration by the horn inside the ultrasonic transducer 32 and the probe 36 disposed on the tip end of the ultrasonic transducer 32, and outputs maximum amplitude via the tip end of the probe 36.

In this state, the probe 36 is inserted into the body via the body wall, that is, the tip end of the probe 36 and the tip end of the probe insertion portion 42 are first stuck into the body wall to prepare a small-diameter hole. In this manner, the ultrasonic trocar system 10 is inserted into the patient's body via the body wall.

Here, a projection length of the tip end 36a of the probe 36 is formed to be comparatively short by a cut portion in a state in which the tip end 36a is inclined by 60 degrees with respect to the axial direction of the probe 36 as compared with a case where the cut angle does not exist. Moreover, the tip end 36a of the probe 36 is not formed at an excessively sharp angle. Therefore, an internal organ is prevented from being damaged as much as possible after the tip end 36a is passed through the peritoneum. Additionally, a portion shown by character α in FIGS. 3A and 3B in a tip end cut processing range has a shape including a certain degree of a peritoneum piercing property, and does not have such an obtuse shape that the peritoneum stretches. Therefore, when the piezoelectric device is ultrasonically vibrated, the punctured hole is safely formed with a very small force by the tip end 36a of the probe 36.

Thereafter, the first hold portion 54 and the second hold portion 64 are held together to perform the dilation. The diameter of the hole formed by the probe 36 is expanded in the vicinity of the outer diameter of the dilator insertion portion 62 of the trocar 60 by the punctured hole dilating portion 58 of the dilator 50. The dilator insertion portion 62 is pressed and guided into the body wall.

After guiding the dilator insertion portion 62 into the body wall, the trocar 60 is held so as to be prevented from moving, and the protrusion 59 of the dilator 50 is disengaged from the rubber seal member 66 of the trocar 60. The unit in which the dilator 50, sheath 40, and handpiece unit 30 are assembled is detached from the through hole of the trocar 60. Therefore, only the trocar 60 is retained in the patient's body wall.

In this state, an endoscope, treatment instrument, and the like are inserted into the trocar 60 to carry out various treatments.

As described above, the following effect is obtained in accordance with the present embodiment.

The first hold portion 54 and second hold portion 64 are formed such that the portions are easily grasped with one hand by the operator and the operation such as the dilation is easily controlled. Therefore, the force at the time of the sticking of the probe 36 into the body wall does not easily fluctuate, or the internal organ is not easily damaged. When the punctured hole is enlarged, stable dilation can be performed. As compared with the dilator 50 including a conventional handle portion, a weight balance is satisfactory, and any projecting portion is not disposed. Therefore, a possibility that the other instruments are hindered can be lowered, and the operator can very stably handle the system.

Therefore, even when the small-diameter hole prepared by the ultrasonic vibration with the probe 36 while preventing bleeding to the utmost is enlarged, the damage onto the body wall can be minimized, when the trocar 60 is introduced. The hole diameter (wound) is reduced, and the trocar 60 can firmly fixed into the body wall during the operation. Therefore, a need for special means for fixing the dilator insertion portion 62 into the body wall such as a separate stopping member can be obviated.

In the present embodiment, the first hold portion 54 having the gourd shape has been described, but any other shape appropriate for the operator such as a columnar shape may also be used as long as the portion is easily held by the operator and the concave portion for fitting the upper end of the second hold portion 64 is disposed in the lower end of the first hold portion. In this case, the operator holds the outer peripheral surface of the columnar first hold portion 54 with the thumb and index finger as if the loop were made, holds the conical second hold portion 64 with the small or third finger, and holds the system appropriately with the other fingers or the palm. At this time, the system is held in a state in which the upper end of the second hold portion 64 is fitted in the concave portion of the lower end of the first hold portion 54, and therefore the system can stably be held.

Next, a second embodiment will be described with reference to FIGS. 4 to 5B. Since this embodiment is a modification example of the first embodiment, the same members as those described in the first embodiment are denoted with the same reference numerals, and the detailed description is omitted.

Figures 5A, 5B:
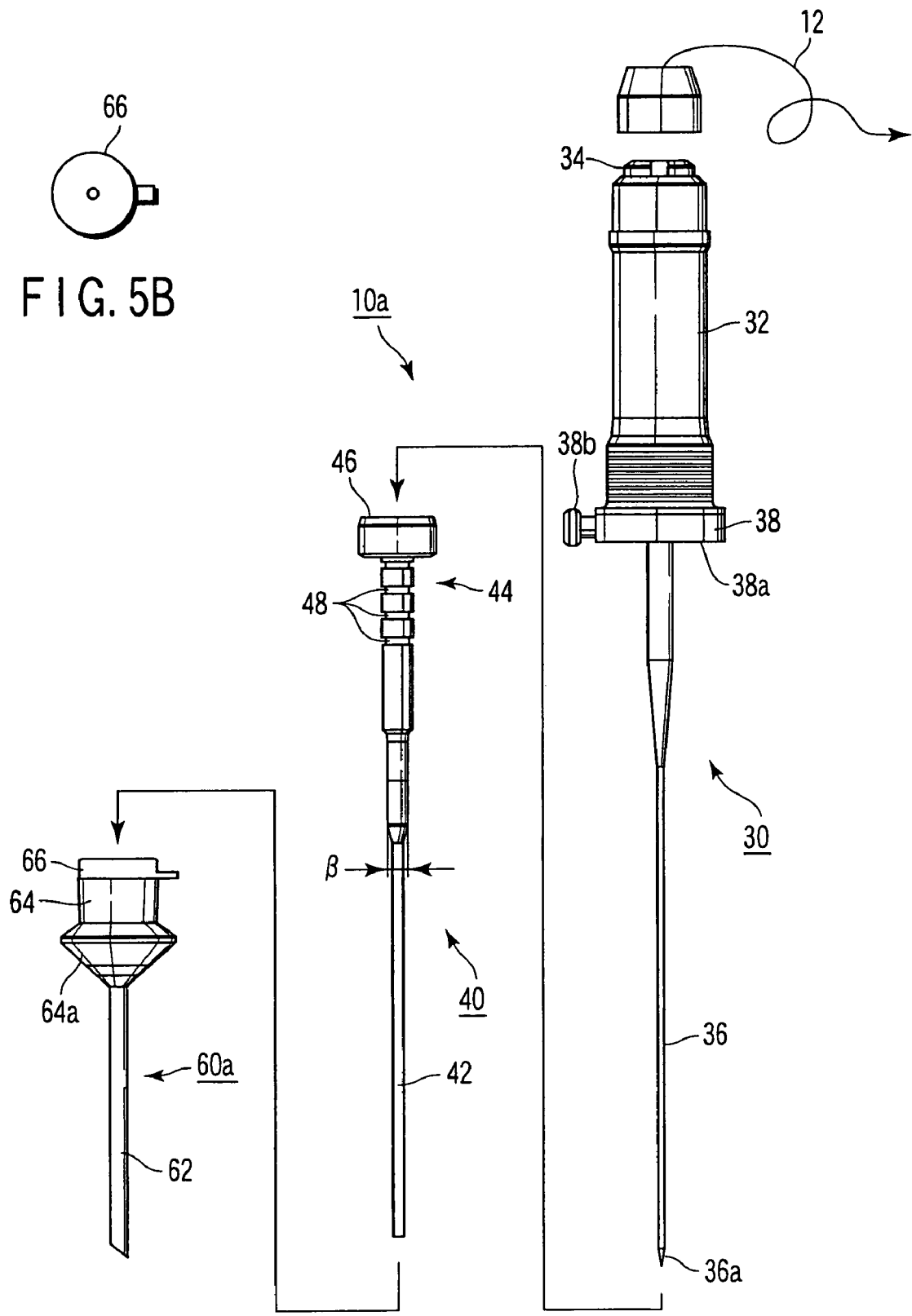
FIG. 5A is a schematic exploded view of the ultrasonic trocar system according to the second embodiment.
FIG. 5B is a top plan view of a trocar shown in FIG. 5A in the ultrasonic trocar system according to the second embodiment.

An ultrasonic trocar system 10a modified with respect to the above-described embodiment using members corresponding to the ultrasonic transducer 32, sheath 40, and small-diameter trocar 60 shown in FIGS. 1 and 2 is shown in FIGS. 4 and 5A.

For a trocar 60a shown in FIGS. 4 and 5A, the inner diameter of the dilator insertion portion 62 is slightly larger than the outer diameter of the probe insertion portion 42. The rubber seal member 66 formed of the rubber material is detachably attached to the upper surface (base end) of the trocar 60a. When the trocar 60a is inserted in the sheath 40, a step portion β of the probe insertion portion 42 is weakly engaged with the seal member 66 of the trocar 60. Therefore, the sheath 40 is substantially fixed-to the trocar 60a via the seal member 66 and step portion β.

The ultrasonic trocar system 10a is usable without disposing the dilator 50 shown in FIGS. 1 and 2 between the sheath 40 and the trocar 60a. For the ultrasonic trocar system 10a, when the outer diameter of the insertion portion 62 is, for example, three millimeters to constitute the small-diameter trocar 60a, and the very small-diameter three-millimeter trocar is combined for use, the dilator 50 is removed to engage the trocar 60a directly with the sheath 40 for use. On the other hand, when a five-millimeter trocar including the insertion portion 62 having an outer diameter of five millimeters is combined for use as the trocar 60 having an inner diameter slightly larger than the outer diameter of the probe insertion portion 42, the system is used in a state in which the dilator 50 is disposed between the sheath 40 and the trocar 60. FIG. 5A shows a constitution for the use of the three-millimeter trocar (trocar 60a).

Next, the operation method (function) will be described using and retaining the three-millimeter trocar 60a in the patient's body wall.

The sheath 40 is attached to the handpiece unit 30. The unit including the assembled sheath 40 and handpiece unit 30 is inserted into the trocar 60a. At this time, the step portion β of the probe insertion portion 42 is weakly engaged with the-rubber seal member 66 of the base end of the trocar 60a.

When the switch 16 (see FIG. 1) of an output control mechanism is operated in this state, the probe 36 is ultrasonically vibrated. A portion denoted with reference numeral 7 in FIG. 4, that is, the portion including the tip end 36a of the probe 36 to the tip end of the trocar 60a is inserted in the patient's body wall. The sheath 40 is used as the shaft to guide the three-millimeter trocar 60a into the body wall via a small punctured hole formed in the body wall.

Thereafter, the step portion β of the probe insertion portion 42 is disengaged from the seal member 66 of the trocar 60 to remove the probe 36 of the handpiece unit 30 and the probe insertion portion 42 from the body wall, and only the trocar 60a is retained in the patient's body wall.

Thereafter, for example, when the trocar 60a having a small outer diameter, for example, the three-millimeter trocar 60a is guided into the body wall, the ultrasonic trocar system 10a in a state in which the dilator is omitted is used to easily insert and retain the trocar 60a in the patient's body wall.

Next, a third embodiment will be described with respect to FIGS. 6 and 7. Since this embodiment is a modification example of the first embodiment, the same members as those described in the first embodiment are denoted with the same reference numerals, and the detailed description is omitted.

As shown in FIG. 6, the constitution of an ultrasonic trocar system 10b according to the present embodiment is substantially the same as that of the first embodiment, but only the shape of a dilator 50b is different.

Figure 7:
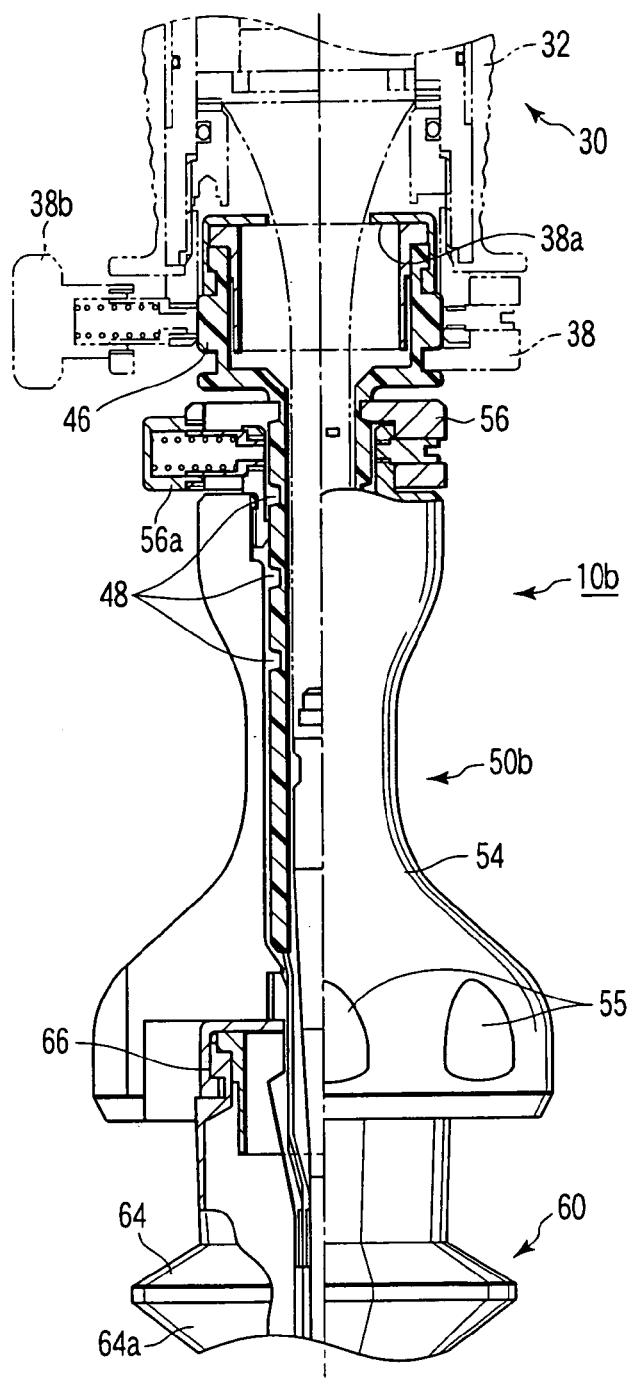
FIG. 7 is a schematic partial sectional view in the vicinity of a dilator hold portion in a state in which constituting members of the ultrasonic trocar system of the third embodiment are mutually assembled.

As shown in FIGS. 6 and 7, a plurality of small holes 55 is arranged in the periphery in the lower end of the hold portion 54 of the dilator 50b. These small holes 55 can be caught by the operator's fingers. Therefore, a grip property (slip stop effect) at the time of the holding of the first hold portion 54 by the operator is enhanced. Even when a plurality of grooves (concave portions) is disposed instead of the small holes 55, the equal effect is obtained.

Additionally, although not shown, the trocar hold portion or the dilator hold portion of the ultrasonic trocar system 10b is not a rotating member which is formed symmetrically with respect to the axial direction of the probe 36, and is formed as a flat member, or may also be shaped to be prevented from rotating and dropping from an operation instrument stand.

Next, a fourth embodiment will be described with reference to FIG. 8. Since this embodiment is a modification example of the first embodiment, the same members as those described in the first embodiment are denoted with the same reference numerals, and the detailed description is omitted.

Figure 8:
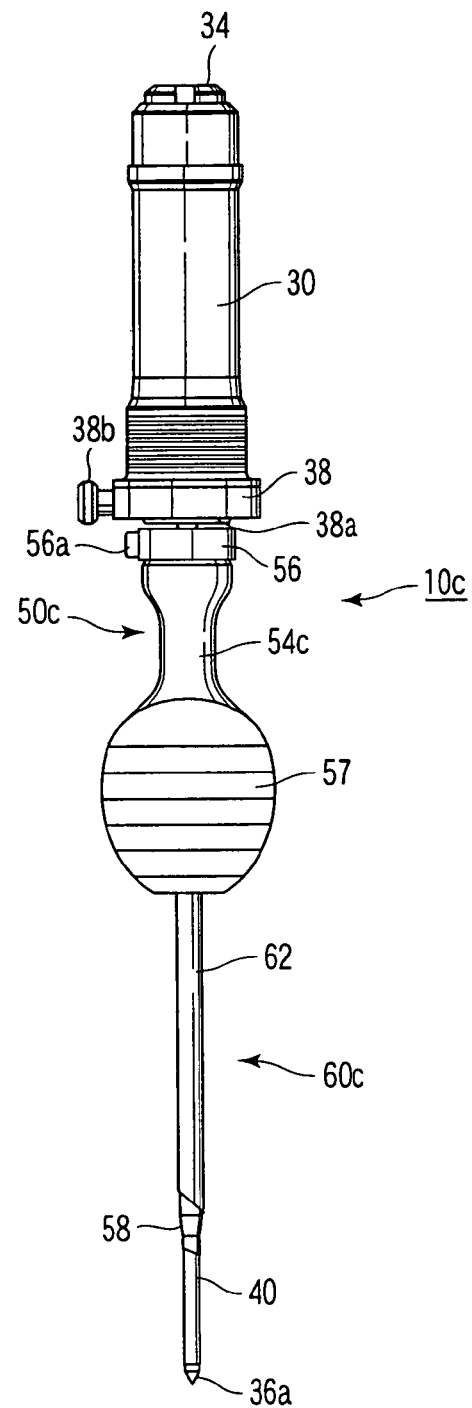
FIG. 8 is a schematic diagram showing the ultrasonic trocar system according to a fourth embodiment.

As shown in FIG. 8, an ultrasonic trocar system 10c of the present embodiment has substantially the same constitution as that of the first embodiment except the shapes of a dilator 50c and trocar 60c.

The tip end (lower end) of a first hold portion 54c of the ultrasonic trocar system 10c is formed as a spherical portion 57 having a substantially large spherical shape. The inside of a main body portion including a hold portion (not shown) of the trocar 60c is completely contained and supported (held) in the spherical portion 57 of the hold portion 54c of the dilator 50c. Therefore, only the dilator insertion portion 62 is observed from the outside of the trocar 60c. When only the constricted portion on the base end of the first hold portion 54c and the spherical portion 57 formed in this shape are grasped, both the dilator 50c and the trocar 60c are simultaneously held. Therefore, the force can more subtly be controlled as compared with the above-described first embodiment.

In the first to fourth embodiments, the ultrasonic transducer 32 including the handpiece unit 30 has been described. That is, the ultrasonic trocar system 10 has been described, but the ultrasonic transducer 32 does not have to be necessarily disposed. That is, when the probe 36 is stuck into the patient's body wall, the probe does not have to be necessarily stuck by the ultrasonic vibration.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general invention concept as defined by the appended claims and their equivalents.

What is claimed is:

1. A trocar system comprising:
    an elongated probe including a first central axis and a tip end configured to be capable of making a puncture hole in living tissue;
    a cylindrical sheath including tip and base ends, a second central axis and a through hole extending along the second central axis between the tip and base ends of the sheath, the sheath being adapted so that the tip end of the probe projects from the tip end of the sheath, when the probe is inserted in the through hole of the sheath and the first central axis is aligned with the second central axis;
    a cylindrical dilator including tip and base ends, a third central axis, a through hole extending along the third central axis between the tip and base ends of the dilator, and a puncture hole dilating portion configured to dilate the puncture hole, formed in the living tissue by the tip end of the probe, at the tip end of the dilator, the dilator being adapted so that the tip end of the sheath projects from the tip end of the dilator, when the sheath is inserted in the through hole of the dilator and the second central axis is aligned with the third central axis;
    a cylindrical trocar including tip and base ends, a fourth central axis and a through hole extending along the fourth central axis between the tip and base ends of the trocar, the trocar being adapted so that the tip end of the dilator projects from the tip end of the trocar, when the dilator is inserted in the through hole of the trocar and the third central axis is aligned with the fourth central axis, with the probe, sheath and dilator being configured to be removable from the through hole of the trocar and the trocar being retained in a patient's body wall, after guiding the trocar between the tip and base ends into the puncture hole formed by the probe;

the trocar system comprising an engaging mechanism configured to detachably engage the dilator with the trocar when the dilator is inserted in the trocar; and wherein:

the trocar comprises a trocar hold portion configured to be held by an operator;

the dilator comprising a dilator insertion portion and a dilator hold portion disposed at the base end of the dilator and configured to be held by the operator;

the dilator hold portion comprising:

a small diameter portion; and a larger diameter portion, the larger diameter portion positioned closer to the dilator insertion portion and having a smooth curved outer surface configured for comfortable gripping and holding of the dilator portion with a palm of one hand of the operator;

the trocar hold portion and the dilator hold portion being interactively configured in a united body, when the trocar is detachably engaged with the dilator, such that the operator is able to grasp and hold both the trocar hold portion and the dilator hold portion with the palm of one hand for one handed puncturing and dilating operation of the trocar system.

2. The trocar system according to claim 1, wherein the dilator hold portion includes: an enlarged diameter portion of the larger diameter portion which is disposed on the base end of the dilator, having an outer diameter enlarged relative to the tip end of the dilator; and the trocar hold portion comprising a bulging portion disposed on the base end of the trocar and formed of at least a part of the base end of the trocar extending in a direction along an axial direction of the trocar toward a side opposite the tip end of the trocar.

3. The trocar system according to claim 2, wherein the enlarged diameter portion includes a concave portion in which at least a portion of the base end of the trocar, on a side opposite the tip end of the trocar, is configured to be fitted.

4. The trocar system according to claim 3, wherein the small diameter portion is configured to be held by the operator's fingers, and the large diameter portion having a diameter progressively enlarged in a direction toward the tip end of the dilator to a diameter larger than the small diameter portion, the large diameter portion being configured to be held by the palm of one hand of the operator.

5. The trocar system according to claim 4, wherein the bulging portion has a conical shape having a small diameter toward the tip end of the trocar and whose diameter is enlarged in a direction extending away from the tip end of the trocar.

6. The trocar system according to claim 5, wherein the probe includes an ultrasonic transducer provided on a base end of the probe, the ultrasonic transducer being configured to be capable of transmitting an ultrasonic vibration and to be capable of oscillating the ultrasonic vibration toward the puncturing tip end of the probe.

7. The trocar system according to claim 6, wherein the puncturing tip end of the probe has a conical shape with a surface of the conical shape being cut away with a planar cut at an acute cut angle with respect to the axial direction of the probe.

8. The trocar system according to claim 7, wherein the cut angle is 60 degrees or less with respect to the axial direction of the probe and the cut extends over a vertical angle of the tip end of the probe.

9. The trocar system according to claim 3, wherein the enlarged diameter portion includes a spherical portion configured to be held by the palm of an operator's hand and the spherical portion includes the concave portion.

10. The trocar system according to claim 9, wherein the bulging portion has a conical shape having a small diameter toward the tip end of the trocar and whose diameter is enlarged in a direction extending away from the tip end of the trocar.

11. The trocar system according to claim 10, wherein the probe includes an ultrasonic transducer provided on a base end of the probe, which is configured to be capable of transmitting an ultrasonic vibration and to be capable of oscillating the ultrasonic vibration toward the tip end of the probe.

12. The trocar system according to claim 11, wherein the puncturing tip end of the probe has a conical shape with a surface of the conical shape being cut away with a planar cut at an acute cut angle with respect to the axial direction of the probe.

13. The trocar system according to claim 12, wherein the cut angle is 60 degrees or less with respect to the axial direction of the probe and the cut extends over a vertical angle of the tip end of the probe.

14. The trocar system according to claim 3, wherein the enlarged diameter portion includes a columnar portion to be held by an operator's hand and the columnar portion includes the concave portion.

15. The trocar system according to claim 14, wherein the bulging portion has a conical shape having a small diameter toward the tip end of the trocar and whose diameter is enlarged in a direction extending away from the tip end of the trocar.

16. The trocar system according to claim 15, wherein the probe includes an ultrasonic transducer provided on a base end of the probe, the ultrasonic transducer being configured to be capable of transmitting an ultrasonic vibration and to be capable of oscillating the ultrasonic vibration toward the tip end of the probe.

17. The trocar system according to claim 16, wherein the puncturing tip end of the probe has a conical shape with a surface of the conical shape being cut away with a planar cut at an acute cut angle with respect to the axial direction of the probe.

18. The trocar system according to claim 17, wherein the cut angle is 60 degrees or less with respect to the axial direction of the probe and the cut extends over a vertical angle of the tip end of the probe.

19. The trocar system according to claim 3, wherein the bulging portion has a conical shape having a small diameter toward the tip end of the trocar and whose diameter is enlarged in a direction extending away from the tip end of the trocar.

20. The trocar system according to claim 19, wherein the probe includes an ultrasonic transducer provided on a base end of the probe, the ultrasonic transducer being configured to be capable of transmitting an ultrasonic vibration and to be capable of oscillating the ultrasonic vibration toward the tip end of the probe.

21. The trocar system according to claim 20, wherein the puncturing tip end of the probe has a conical shape with a surface of the conical shape being cut away with a planar cut at an acute cut angle with respect to the axial direction of the probe.

22. The trocar system according to claim 21, wherein the cut angle is 60 degrees or less with respect to the axial direction of the probe and the cut extends over a vertical angle of the tip end of the probe.

23. The trocar system according to claim 1, wherein the united body of trocar and dilator hold portions includes at least one slip stopping element which prevents the united body of hold portions from slipping from the operator's hand.

24. The trocar system according to claim 1, wherein the probe includes an ultrasonic transducer provided on a base end of the probe, the ultrasonic transducer being configured to be capable of transmitting an ultrasonic vibration and to be capable of oscillating the ultrasonic vibration toward the tip end of the probe.

25. The trocar system according to claim 24, wherein the puncturing tip end of the probe has a conical shape with a surface of the conical shape being cut away with a planar cut at an acute cut angle with respect to the axial direction of the probe.

26. The trocar system according to claim 25, wherein the cut angle is 60 degrees or less with respect to the axial direction of the probe and the cut extends over a vertical angle of the tip end of the probe.

27. The trocar system according to claim 1, wherein the puncturing tip end of the probe has a conical shape with a surface of the conical shape being cut away with a planar cut at an acute cut angle with respect to the axial direction of the probe.

28. The trocar system according to claim 27, wherein the cut angle is 60 degrees or less with respect to the axial direction of the probe and the cut extends over a vertical angle of the tip end of the probe.

29. A trocar system comprising:
an elongated probe which includes a first central axis and a tip end configured to be capable of making a puncture hole in a living tissue;
a cylindrical sheath including tip and base ends, a second central axis and a through hole extending along the second central axis between the tip and base ends of the sheath, the sheath being adapted so that the tip end of the probe projects from the tip end of the sheath, when the probe is inserted in the through hole of the sheath align and the first central axis is aligned with the second central axis; a cylindrical sheath insertion portion including tip and base ends, a third central axis, a through hole extending along the third central axis between the tip and base ends of the sheath insertion portion, and a puncture hole dilating portion to dilate the punctured hole, formed in the living tissue by the tip end of the probe, in the tip end of the sheath insertion portion, the sheath insertion portion being adapted so that the tip end of the sheath projects from the tip end of the sheath insertion portion, when the sheath is inserted in the through hole of the sheath insertion portion and the second central axis is aligned with the third central axis;
a cylindrical dilator insertion portion which includes tip and base ends, a fourth central axis, and a through hole extending along the fourth central axis between the tip and base ends, the dilator insertion portion being adapted so that the tip end of the sheath insertion portion projects from the tip end of the dilator insertion portion, when the sheath insertion portion is inserted in the through hole of the dilator insertion portion and the third central axis is aligned with the fourth central axis,
with the probe, sheath and sheath insertion portion configured to be removable from the through hole of the dilator insertion portion to retain the dilator insertion portion in a patient's body wall, after guiding the dilator insertion portion between the tip and base ends into the punctured hole; a dilator hold portion disposed on the base end of the sheath insertion portion and configured to be held by the operator with the sheath insertion portion inserted in the dilator insertion portion and having an outer diameter enlarged relative to the tip end of the sheath insertion portion; and
a trocar hold portion disposed on the base end of the dilator insertion portion and configured to be held by the operator with the sheath insertion portion inserted in the dilator insertion portion, the trocar hold portion having a portion toward the tip end of the dilator insertion portion which bulges in a direction away from the axis of the dilator insertion portion, and a portion on at least a side opposite the tip end of the dilator insertion portion being held by the dilator hold portion when the sheath insertion portion is inserted in the dilator insertion portion;
the trocar hold portion being configured such that the operator is able to grasp and hold both the trocar hold portion and the dilator hold portion with the palm of one hand in one united hold portion body when the trocar hold portion is detachably engaged with the dilator hold portion, for one handed puncturing and dilating operation of the trocar system.

30. The trocar system according to claim 29, wherein the dilator hold portion includes an enlarged diameter portion whose diameter is enlarged relative to the tip end of the sheath insertion portion, and the trocar hold portion includes a bulging portion which extends in a direction extending along the axial direction of the dilator insertion portion toward a side of the trocar hold portion opposite the tip end of the dilator insertion portion, at least a part of the trocar held portion being covered with the dilator hold portion when the sheath insertion portion is inserted in the dilator insertion portion.

31. The trocar system according to claim 30, wherein the enlarged diameter portion includes a small diameter portion configured to be held by the operator's fingers, and a large diameter portion whose diameter is progressively enlarged in a direction toward the tip end of the sheath insertion portion to a diameter larger than the small diameter portion, and the enlarged diameter portion being configured to be held by the palm of one hand of the operator.

32. The trocar system according to claim 31, wherein the bulging portion has a conical shape having a small diameter toward the tip end of the dilator insertion portion and whose diameter is enlarged in a direction extending away from the tip end of the dilator insertion portion.

33. The trocar system according to claim 32, wherein the probe includes an ultrasonic transducer provided on a base end of the probe, the ultrasonic transducer being configured to be capable of transmitting an ultrasonic vibration and to be capable of oscillating the ultrasonic vibration toward the tip end of the probe.

34. The trocar system according to claim 33, wherein the puncturing tip end of the probe has a conical shape with a surface of the conical shape being cut away at an acute cut angle with respect to the axial direction of the probe.

35. The trocar system according to claim 34, wherein the cut angle is 60 degrees or less with respect to the axial direction of the probe and the cut extends over a vertical angle of the tip end of the probe.

36. The trocar system according to claim 30, wherein the enlarged diameter portion includes a spherical portion to be held by an operator's palm of one hand and the spherical portion includes the concave portion.

37. The trocar system according to claim 36, wherein the bulging portion has a conical shape having a small diameter toward the tip end of the dilator insertion portion and whose diameter is enlarged in a direction extending away from the tip end of the dilator insertion portion.

38. The trocar system according to claim 37, wherein the probe includes an ultrasonic transducer provided on a base end of the probe, the ultrasonic transducer being configured to be capable of transmitting an ultrasonic vibration and to be capable of oscillating the ultrasonic vibration toward the tip end of the probe.

39. The trocar system according to claim 38, wherein the puncturing tip end of the probe has a conical shape with a surface of the conical shape being cut away at an acute cut angle with respect to the axial direction of the probe.

40. The trocar system according to claim 39, wherein the cut angle is 60 degrees or less with respect to the axial direction of the probe and the cut extends over a vertical angle of the tip end of the probe.

41. The trocar system according to claim 30, wherein the enlarged diameter portion includes a spherical portion to be held by an operator's palm of one hand and the spherical portion includes the concave portion.

42. The trocar system according to claim 41, wherein the bulging portion has a conical shape having a small diameter toward the tip end of the dilator insertion portion and whose diameter is enlarged in a direction extending away from the tip end of the dilator insertion portion.

43. The trocar system according to claim 42, wherein the probe includes an ultrasonic transducer provided on a base end of the probe, the ultrasonic transducer being configured to be capable of transmitting an ultrasonic vibration and to be capable of oscillating the ultrasonic vibration toward the tip end of the probe.

44. The trocar system according to claim 43, wherein the puncturing tip end of the probe has a conical shape with a surface of the conical shape being cut away with a planar cut at an acute cut angle with respect to the axial direction of the probe.

45. The trocar system according to claim 44, wherein the cut angle is 60 degrees or less with respect to the axial direction of the probe and the cut extends over a vertical angle of the tip end of the probe.

46. The trocar system according to claim 30, wherein the enlarged diameter portion includes a spherical portion to be held by an operator's palm of one hand and the spherical portion includes the concave portion.

47. The trocar system according to claim 46, wherein the probe includes an ultrasonic transducer provided on a base end of the probe, the ultrasonic transducer being configured to be capable of transmitting an ultrasonic vibration and to be capable of oscillating the ultrasonic vibration toward the tip end of the probe.

48. The trocar system according to claim 47, wherein the puncturing tip end of the probe has a conical shape with a surface of the conical shape being cut away with a planar cut at an acute cut angle with respect to the axial direction of the probe.

49. The trocar system according to claim 48, wherein the cut angle is 60 degrees or less with respect to the axial direction of the probe and the cut extends over a vertical angle of the tip end of the probe.

50. The trocar system according to claim 29, wherein the united hold portion body includes at least one slip stopping element which prevents the united hold portion body from slipping from the operator's hand.

51. The trocar system according to claim 29, wherein the probe includes an ultrasonic transducer provided on a base end of the probe, the ultrasonic transducer being configured to be capable of transmitting an ultrasonic vibration and to be capable of oscillating the ultrasonic vibration toward the tip end of the probe.

52. The trocar system according to claim 51, wherein the puncturing tip end of the probe has a conical shape with a surface of the conical shape being cut away with a planar cut at an acute cut angle with respect to the axial direction of the probe.

53. The trocar system according to claim 52, wherein the cut angle is 60 degrees or less with respect to the axial direction of the probe and the cut extends over a vertical angle of the tip end of the probe.

54. The trocar system according to claim 29, wherein the puncturing tip end of the probe has a conical shape with a surface of the conical shape being cut away with a planar cut at an acute cut angle with respect to the axial direction of the probe.

55. The trocar system according to claim 54, wherein the cut angle is 60 degrees or less with respect to the axial direction of the probe and the cut extends over a vertical angle of the tip end of the probe.

* * * * *